United States Patent [19]

Mardorf et al.

[11] Patent Number: 4,465,474
[45] Date of Patent: Aug. 14, 1984

[54] INJECTOR FOR MEDICAL USES HAVING AN IMPROVED AUTOMATIC SWITCH-OFF SYSTEM

[75] Inventors: Robert Mardorf; Sigfried Hebberg, both of Melsungen, Fed. Rep. of Germany

[73] Assignee: Intermedicat GmbH, Emmenbrücke, Switzerland

[21] Appl. No.: 450,738

[22] Filed: Dec. 17, 1982

[30] Foreign Application Priority Data

Dec. 21, 1981 [DE] Fed. Rep. of Germany ... 8137235[U]

[51] Int. Cl.³ .............................................. A61M 5/20
[52] U.S. Cl. ............................. 604/154; 128/DIG. 1
[58] Field of Search ..................... 604/154, 155, 131; 128/DIG. 1

[56] References Cited

U.S. PATENT DOCUMENTS

| | | | |
|---|---|---|---|
| 3,701,350 | 10/1972 | Guenther | 604/155 X |
| 4,108,177 | 8/1978 | Pistor | 604/155 |
| 4,191,187 | 3/1980 | Wright | 128/DIG. 1 X |

*Primary Examiner*—Stephen C. Pellegrino
*Attorney, Agent, or Firm*—Kenyon & Kenyon

[57] ABSTRACT

An injector for medical uses comprises a housing (30) on which a first holder (65) for holding the front end of a syringe (13) is movably mounted. A slide (32) is movable relative to the housing (30). A second holder (66) for attachment of the syringe piston (14) is mounted to the slide (32). When the force exerted by the syringe cylinder (12) on the first holder (65) reaches an overload condition, the first holder (65) moves counter to the action of a spring (58). An actuating element (62) connected to first holder (65) then actuates a switch (48) whereby the motor drive of the slide (32) is turned off.

9 Claims, 5 Drawing Figures

INJECTOR FOR MEDICAL USES HAVING AN IMPROVED AUTOMATIC SWITCH-OFF SYSTEM

FIELD OF THE INVENTION

This invention relates to an injector for medical uses. More particularly, this invention relates to an injector for medical uses comprising a housing, a first holder mounted to said housing for attachment of the cylinder of a syringe, a motor driven slide which is displaceable relative to the housing and which has a second holder mounted thereon for attachment of the piston rod of the syringe, and a switch disposed on the housing which is actuated by an actuating element connected with the slide for turning the motor off at the maximum mutual approach of the first and second holders.

BACKGROUND OF THE INVENTION

Injectors of the type to which the present invention is directed (such injections sometimes being referred to as "pressure infusion apparatus") are used for infusing a liquid medication into a patient by means of a syringe in a uniform manner over an extended period of time, e.g. 24 hours. This requires the discharge of minute volumes of liquid, e.g., 0.06 to 6 ml/h, at a substantially constant infusion rate under conditions of the strictest sterility. The velocity deviation is generally limited to about 1%. The use of highly active drugs requires not only a very constant dosage rate but also an alarm signal to alert attending medical personnel in the event the infusion ends or is interrupted.

In medical injectors, the path travelled by the second holder of the injector which moves the syringe piston is limited by the length of the syringe. Accordingly, it is known practice to equip the injector with a limit switch which, when the syringe has been squeezed empty, turns off the motor that moves the injector's slide. Such automatic switching off of the injector is thus dependent on the length of path travelled by the injector's slide. Because of the manufacturing tolerances of the injector and of the syringe, a safety reserve of the drug must be maintained in the syringe so that the switching off takes place prior to the syringe being completely emptied. Therefore, a residual amount of the drug remains in the syringe. This is a particularly great disadvantage in the case of expensive drugs.

Another problem that occurs with the use of injectors is that the tube connecting the syringe to a patient may become blocked for some reason. For example, the tube may be accidentally pinched. In this situation, the syringe works against a high flow resistance which may result in the syringe piston becoming deformed. This is particularly a problem with single-use syringes which are made of plastic. As a result, the patient does not receive the needed quantity of the drug infusion even though the injector appears to be operating properly. Finally, this condition may lead to overload of the injector. For this reason, overload safety devices have been developed. In the event of an inadmissably high pressure build-up in the syringe, these overload safety devices signal an alarm or cause the injector's motor to switch off.

OBJECT OF THE INVENTION

It is therefore an object of the present invention to provide an injector for medical uses having a safety system wherein the path-dependent limit switch-off and the load-dependent switch-off and alarm are combined with one another in order to simplify the instrumentation and to make the injector operationally more reliable.

These and other objects will be apparent from the following description and claims in conjunction with the drawings.

SUMMARY OF THE INVENTION

To solve these problems of the prior art, the medical injector of the present invention comprises a first syringe holder movably mounted on the injector housing for movement parallel to the direction of movement of the injector slide. The first syringe holder is biased to prevent movement in the direction of movement of the second syringe holder towards the first syringe holder preferably by a tensioning device until a pressure overload occurs in the liquid transport system. An actuating element is connected to the first syringe holder which actuates the motor turn off switch upon movement of the first syringe holder counter to the action of the tensioning device.

The present invention may be generally summarized as an injector for medical uses comprising a housing, a first holder mounted to said housing for attachment of a cylinder of a syringe, a motor driven slide movably mounted to said housing for displacement relative to said housing in a first direction toward said first holder and in an opposite second direction away from said first holder, a second holder mounted to said slide for attachment to a piston of said syringe wherein displacement of said slide results in corresponding displacement of said second holder, switching means for turning off said motor wherein said switching means is actuated by first actuating means responsive to the movement of said slide to a selected position corresponding to the maximum mutual approach of said first and second holders; the improvement comprising:

said first holder is movably mounted to said housing for movement relative to said housing parallel to the direction of movement of said slide;

second actuating means connected to said first holder for displacement therewith wherein said switching means is actuated by said second actuating means upon displacement of said first holder a selected distance in said first direction;

resilient means connected to said housing and said first holder for applying a selected force to said first holder for preventing displacement of said first holder relative to said housing in said first direction; wherein applying a force greater than said selected force to said first holder in said first direction causes restrained movement of said first holder in said first direction counter to said resilient means force whereby upon displacement of said first holder said selected distance in said first direction said switching means is actuated by said second actuation means.

BRIEF DESCRIPTION OF THE DRAWING

In the drawing forming part hereof.

DESCRIPTION OF THE PREFERRED EMBODIMENTS

In order to afford a more complete understanding of the present invention and an appreciation of its advantages, a description of the preferred embodiments is presented below.

In accordance with the preferred embodiment of the present invention, the same switch is used for the path-dependent limit switch-off and for the load-dependent overload switch-off. The overload switch-off of the injector's motor takes place when the infusion solution can no longer flow out of the syringe. The overload switch-off also takes place when for any reason the path-dependent switch-off fails to occur at the end of the syringe piston movement.

The limit switch-off responds immediately when the syringe piston reaches a selected piston position with respect to the syringe cylinder. The overload switch-off reacts with a certain time delay. In the case of overload, the tensioning device must first be tensioned. The advantage of this is that brief overloads caused, for example, by the temporary pinching of the tube connected to the syringe and leading to the patient, do not trigger the overload switch-off and corresponding alarm.

Figure 2:
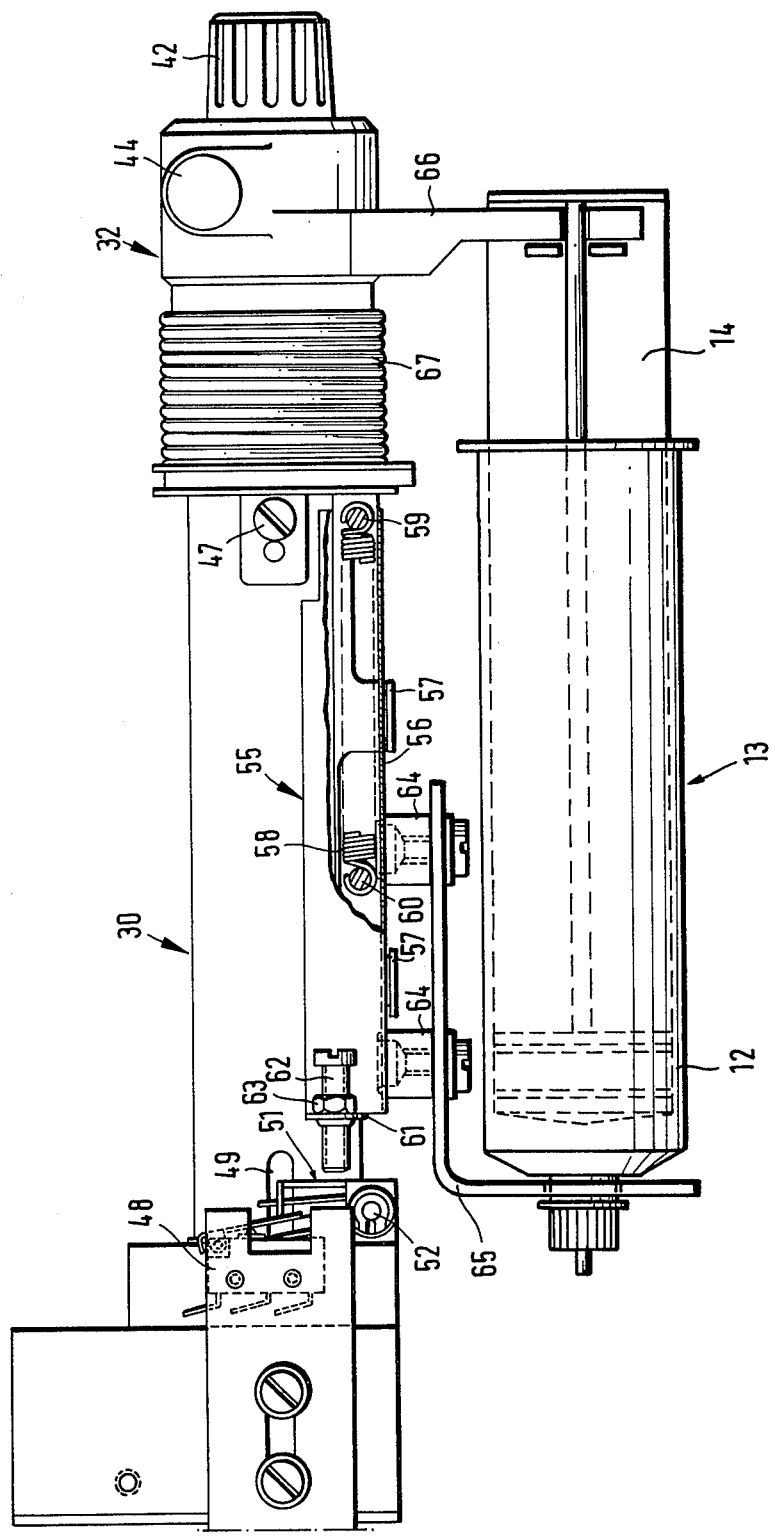
FIG. 2 is a side elevation view with parts broken away of an injector for medical uses in accordance with another embodiment of the present invention.

According to a preferred embodiment of the invention and with reference to FIG. 2, the first holder 65 and the additional actuating element 62 are fastened to a guide member 55 which is movably mounted on the injector housing 30 for lengthwise displacement. The displacement of guide member 55 is restrained under the action of the tensioning device 58 which has one end engaging the guide member 55 and another end engaging the housing 30.

The additional actuating element, in accordance with the present invention, is preferably an adjustable screw as illustrated in FIG. 2. By adjustment of this screw, mutual adaptation between the system of the path-dependent switch-off and the overload system is possible. It is further possible to adjust the force and hence the respective length of the path travelled by guide member 55 at which the overload safety device trips.

According to a preferred embodiment of the present invention, both the path-dependent and overload actuating elements act on a common lever which is biased, for example, by a tension spring, away from the contact element of the single switch. The functions of the path-dependent limit switch-off and of the overload safety device are combined by their common lever.

A special advantage of the present invention is that a single switch is actuated for turning the motor off as a function of two different operational parameters. This results in a reduced cost of instrumentation and a simplification of the injector.

Various embodiments of the present invention are now more specifically explained with reference to the drawings.

Figure 1:
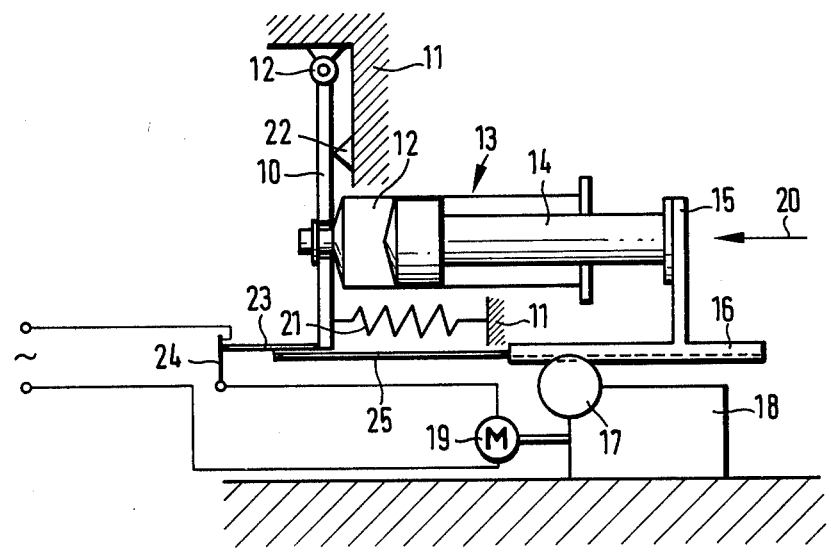
FIG. 1 is a side elevation schematic representation of an injector for medical uses in accordance with one embodiment of the present invention.

The injector, as shown schematically in FIG. 1, comprises a first holder 10 which is secured to a housing 11 through a pivot joint 12. The mouthpiece of the cylinder 12 of a syringe 13 is inserted in first holder 10 so that cylinder 12 is fixed relative to first holder 10.

The rear end of the piston rod 14 of syringe 13 is mounted to a second holder 15. Second holder 15 is movable parallel to syringe 13 by means of a linear drive. The linear drive may comprise a rack 16 which is driven by an electric motor 19 through a gear or worm wheel 17 and a transmission 18. Piston rod 14 is moved by the second holder 15 in the direction of arrow 20, whereby a liquid contained in syringe 13 is slowly and continuously squeezed out of the syringe 13.

The first holder 10 is a lever which is engaged at its free end by a spring 21. The other end of spring 21 is fastened to the housing 11. Spring 21, which is an extension spring, has an initial tension strong enough to pull the holder 10 against the stop 22 of housing 11 during the normal evacuation of the syringe 13. If the force exerted by cylinder 12 on holder 10 exceeds the permissible amount, spring 21 is stretched, and holder 10 is swiveled or pivoted about the joint 12. Upon this swivel movement, a rod 23 connected with the free end of holder 10 actuates a switch 24. Switch 24 is normally closed and lies in the power supply circuit of motor 19. In case of overload, switch 24 is opened via road 23 through the movement of lever 10 so that motor 19 is turned off. An acoustic and/or optical alarm (not shown) may also be provided which is set off at the same time motor 19 is turned off.

Switch 24 is acted upon by another actuating element in the form of a rod 25 which is connected to the rack 16 or alternately the second holder 15. Rod 25 has a length selected so that its end opens switch 24 when the piston of syringe 13 has reached the front end position in cylinder 12. Thus, the two actuating elements 23, 25 act independently of each other on the single switch 24. That is, each of the two actuating elements is able, independent of the other actuating element, to open the normally closed switch 24 in order to interrupt the power supply circuit of motor 19.

Figure 3:
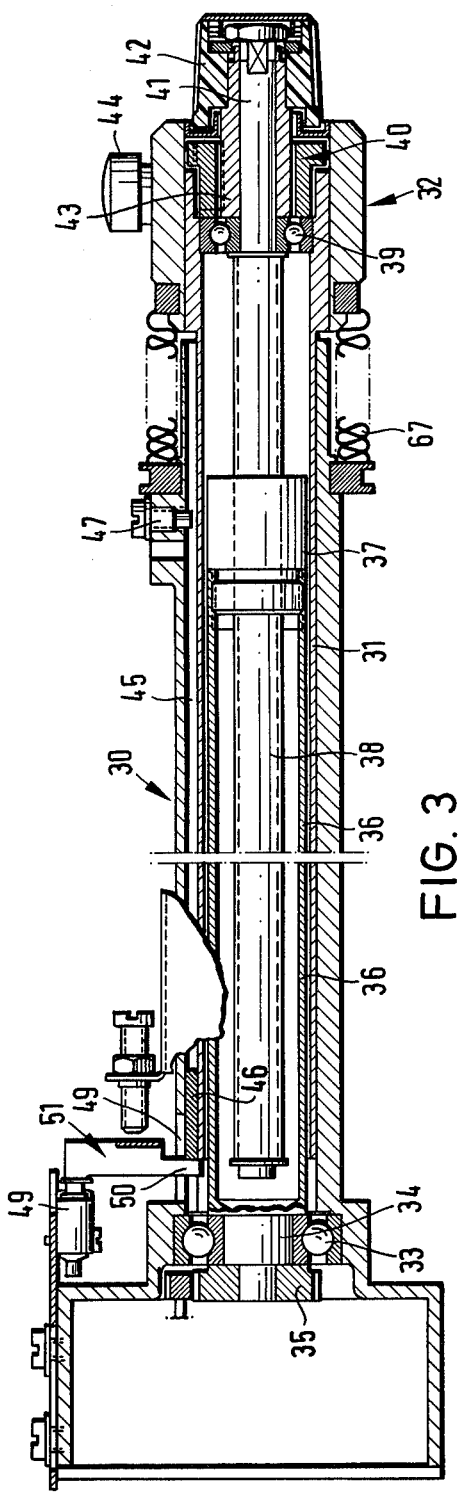
FIG. 3 is a longitudinal cross sectional view of a portion of the embodiment of the injector in accordance with the invention illustrated in FIG. 2.
Figure 4:
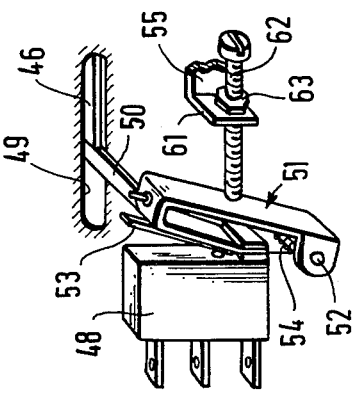
FIG. 4 is a perspective view of a switching device useful in the embodiments of the injector according to the present invention illustrated FIGS. 2 and 3.

Another embodiment of the injector, in accordance with the present invention, is illustrated in FIGS. 2 to 4. Referring to FIG. 3, the housing 30 comprises a pipe-like structure in which a sleeve 31 is disposed for lengthwise displacement. Sleeve 31 is firmly connected with slide 32. At one end of housing 30, shaft piece 34 is mounted by ball bearings 33. Shaft piece 34 is connected at one end with a gear 35 and at its other end with a pipe 36 extending coaxially within housing 30. Gear 35 is driven by the motor (not shown) through a pinion, whereby it drives the pipe 36. The front end of pipe 36 is firmly jointed to nut 37 of a ball gear train. Nut 37 sits on a spindle 38. Spindle 38 is mounted in slide 32 by a ball bearings 39 and extends coaxially in pipe 36. The ball gear train comprising nut 37 and spindle 38 corresponds to that disclosed in DE-OS No. 14 25 787 and is not described in detail herein. The disclosure of DE-OS No. 14 25 787 is incorporated herein by reference. Such a ball gear train is non-self-locking. That is, it is possible, with pipe 36 retained in place, to move the spindle 38 by linear movement of slide 32 relative to nut 37, in which event, however, spindle 38 rotates. It will be appreciated, that when the motor is turned off, pipe 36 will be held in place by the motor and nut 37 will be held in place by pipe 36.

The end of spindle 38 is connected, via a shaft piece 41 fixed to the spindle, with a rotary knob 42 which protrudes from slide 32. Rotary knob 42 enables spindle 28 to be turned by hand. Mounted on the shaft-piece 41 is a bushing 43 which is fixed thereto and which is connectable with the housing of slide 32 through a freewheeling clutch 40. The freewheeling clutch 40 is of a similar design as a bicycle freewheeling mechanism. It contains needles (not shown) which permit rotation of spindle 38 only in the direction in which the syringe is squeezed out and not in the opposite direction when the spindle 38 is connected to the slide by the freewheeling mechanism 40. The freewheeling mechanism 40 has a release which is actuated by a push button 44. When button 44 is pushed, spindle 38 is completely uncoupled from slide 40 so that slide 40 can be linearly displaced in both directions. When this occurs, spindle 38 rotates in the held in place nut 37. During depression of button 44, therefore, slide 32 can be adjusted to the desired position. Thereafter, when button 44 is released, a fine adjustment of the slide 32 can be effected by turning the rotary knob 42. However, the fine adjustment can only be made in the direction in which sleeve 31 is moved linearly into housing 30, not in the opposite direction. This is because the freewheeling mechanism has connected spindle 38 to the slide 32 and now only permits rotation of spindle 38 in the direction which permits slide 32 to be displaced into the housing 30. When thereafter the motor is turned on, pipe 36 will rotate together with nut 37, whereby slide 32, which is secured against rotation relative to housing 30, is displaced linearly into the housing 30. A more detailed description of the ball gear drive and freewheeling mechanism of the embodiment of the injector of FIG. 3, may be found in copending U.S. Patent Application Ser. No. 447,968 filed Dec. 8, 1982 in the name of Robert Mardoff and Sigfried Hessberg entitled Injector for Medical Uses the disclosure of which is incorporated herein by reference.

In its interior, housing 30 has a lengthwise groove 45. The actuating element 46 fastened at the left end of sleeve 31 is displaceable in groove 45 upon displacement of sleeve 31 which is connected to slide 32. The actuating element 46 comprises a strip type metal piece which extends at the left end of sleeve 31. It fulfills several functions: Actuating element 46 locks sleeve 31 and hence slide 32 against rotation relative to housing 30 because it is mounted in groove 45. It acts by its right edge as an abutment element to prevent extraction of slide 32 from the housing. Upon extraction of slide 32 to its limit, actuating element 46 abuts, against a screw 47 secured on housing 30 and protruding into the longitudinal groove 45 thus preventing further extraction of slide 32. In addition, actuating element 46 causes the actuation of switch 48 when the left end position of slide 32 is reached.

At the point in which the left end of the actuating element 46 is in the left end position of slide 32, housing 30 has a slot 49 into which the shoulder 50 of a lever 51 projects from the exterior of housing 30. With reference to FIG. 4, lever 51 is pivotally mounted on axle 52 which extends horizontally and is parallel to the shoulder 50. Lever 51 is pivoted by the actuating element 46 about its axle 52. Lever 51 thereby actuates the contact arm 53 of switch 48 which lies in the power supply circuit of the motor and is normally closed.

Mounted on the axle 52 of lever 51 is a spring 54 which pushes or biases lever 51 away from contact arm 53. The actuation of switch 48 by the actuating element 46 occurs counter to the tension of spring 54. In the embodiment illustrated in FIG. 3, switch 48 and its component parts is mounted external to housing 30.

Referring to FIG. 2, a guide member 55 is movably mounted on the underside of housing 30 for lengthwise displacement. Guide member 55 comprises a U-shaped plate, the base plate 56 of which has elongated guide holes through which protrude projections 57 of housing 30. A tensioning device tensions the guide member 55 in the direction of slide 32 (to the right) and comprises two springs 58 only one of which is shown in FIG. 2. The springs 58 are extension springs. One end of springs 58 is connected to pin 59 mounted on the housing 30. The other end of springs 58 is connected to a pin 60 which extends between the legs of the guide member 55 and is firmly connected therewith. At its left end, the guide member 55 has a bracket 61 bent at right angles to housing 30. The second actuating element, comprising a screw 62, passes through bracket 61 of guide member 55 and is oriented parallel to the axis of housing 30. Screw 62 is screwed through a thread in bracket 61. A lock nut 63 is fitted on screw 62. The (left) free end of screw 62 is adapted to push against lever 51 and drive lever 51 against the contact arm 53 of switch 48 counter to the action of spring 54.

In the embodiment of FIG. 2, the first holder 65 is fastened to the base plate 56 of the guide member 55 by pedestal elements 64. First holder 65 comprises an L-shaped part, the free leg of which extends downward as shown in FIG. 2. Free leg 65 has a lateral recess into which the neck of syringe 13 is inserted. The piston rod 14 of syringe 13 is inserted in a recess of the second holder 66 which is mounted to and extends downward from the slide 32. Bellows 67 is connected between slide 32 and housing 30. Bellows 67 covers the portion of sleeve 31 projecting from housing 30 determined by the extended length of slide 32.

As shown in FIG. 4, lever 51 is a one-armed lever. Screw 62 is closer to the axle 52 of the lever than is the projection 50. For this reason, the path which screw 62 must travel to carry out the switching process is shorter than the path which the projection 50 must travel. This leads to a short switching path for the overload switch-off and to a correspondingly longer switching path of the path-dependent switch-off which results in the possibility of very precise fixing of the switch-off position.

When a counter-pressure occurs in syringe 13, as may happen, for example, if the tubing connected with the mouthpiece of the syringe is pinched, the bracing force exerted by cylinder 12 on the first holder 65 increases. As this force increase the initial tension of the springs 58 will eventually be exceeded and the guide member 55 will be displaced to the left relative to the housing 30. The actuating element 62 then pivots lever 51 which actuates switch 48 to turn the motor off.

Figure 5:
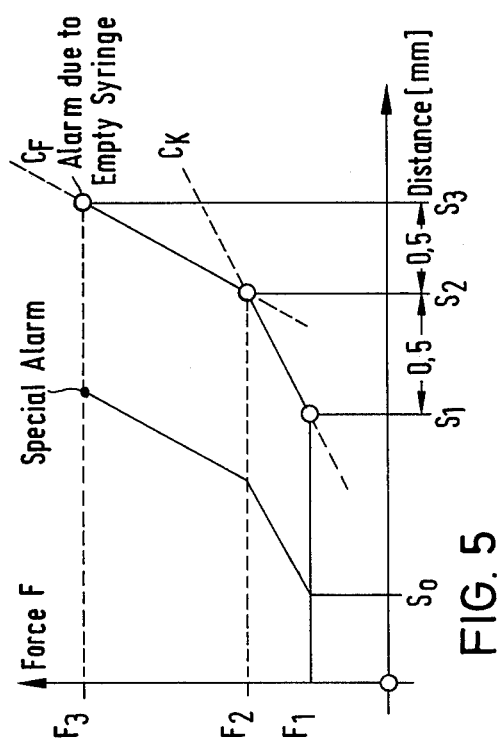
FIG. 5 is a graph of the load-dependent switch-off process in accordance with the present invention wherein the path of an injector slide is plotted on the abscissa and the force acting on the first syringe holder of the injector is plotted on the ordinate.

The load-dependent switch-off process is illustrated in FIG. 5 where the path of slide 32 is plotted along the abscissa and the force acting on the first holder 65 along the ordinate.

Force $F_1$ is necessary for carrying out the infusion along the total path (piston stroke of the syringe). $F_1$, therefore, is the sum of the friction force of syringe 13 and the force for overcoming the flow resistances in the liquid system. As soon as the liquid system is blocked, piston rod 14 begins to deform elastically. The spring constant of piston rod 14 is $C_k$. The force $F_2$ builds up by which cylinder 12 of syringe 13 is pressed against the first holder 65. After this force $F_2$ has been overcome, the springs 58 are tensioned further. Now the switch-off path of switch 48 (which may be, e.g., 0.5 mm) must be traveled before the motor is turned off as force $F_3$ is reached.

Whereas the pressure switch-off occurs with a corresponding time delay whenever too great a counterpressure occurs in the system, the path-dependent switch-off by actuating element 46 always reacts exactly upon slide 32 reaching a selected intended position or respectively upon piston 14 reaching a selected piston stroke in syringe 13. By this type of path switch-off, the injector is protected against the use of syringes which are too short. It cannot jam or bind. On the other hand, the pressure-dependent switch-off arrangement offers protection against the use of syringes which are too long.

Although preferred embodiments of the present invention have been described in detail, it is contemplated that modifications may be made within the spirit and the scope of the invention. It will be appreciated that variations in the details of the mechanical design of the present invention may be readily made by one skilled in the art.

What is claimed is:

1. In an injector for medical uses comprising a housing, a first holder mounted to said housing for attachment of a cylinder of a syringe, a motor driven slide movably mounted to said housing for displacement relative to said housing in a first direction toward said first holder and in an opposite second direction away from said first holder, a second holder mounted to said slide for attachment to a piston of said syringe wherein displacement of said slide results in corresponding displacement of said second holder, switching means for turning off said motor wherein said switching means is actuated by first actuating means responsive to the movement of said slide to a selected position corresponding to the maximum mutual approach of said first and second holders; the improvement comprising:
   said first holder is movably mounted to said housing for movement relative to said housing parallel to the direction of movement of said slide;
   second actuating means connected to said first holder for displacement therewith wherein said switching means is actuated by said second actuating means upon displacement of said first holder a selected distance in said first direction;
   resilient means connected to said housing and said first holder for applying a selected force to said first holder for preventing displacement of said first holder relative to said housing in said first direction; wherein,
   applying a force greater than said selected force to said first holder in said first direction causes movement of said first holder in said first direction counter to said resilient means force whereby upon displacement of said first holder said selected distance in said first direction said switching means is actuated by said second actuation means.

2. An injector as recited in claim 1 further comprising:
   a guide member movably mounted to said housing for movement relative to said housing parallel to the direction of movement of said slide; wherein,
   said first holder is fixedly mounted to said guide member; and,
   said resilient means is connected to said housing and said guide member.

3. An injector as recited in claim 2 wherein said second actuating means comprises an adjustable screw member.

4. An injector as recited in claim 3 wherein said switching means comprises:
   a switching element;
   one lever member pivotally mounted adjacent to said switching element for contacting said switching element for turning off said motor;
   means for biasing said lever member away from contact with said switching element, wherein said first actuating means and said second actuating means act upon said one lever member.

5. An injector as recited in claim 2 wherein said switching means comprises:
   a switching element;
   one lever member pivotally mounted adjacent to said switching element for contacting said switching element for turning off said motor;
   means for biasing said lever member away from contact with said switching element, wherein said first actuating means and said second actuating means act upon said one lever member.

6. An injector as recited in claim 1 wherein said second actuating means comprises an adjustable screw member.

7. An injector as recited in claim 6 wherein said switching means comprises:
   a switching element;
   one lever member pivotally mounted adjacent to said switching element for contacting said switching element for turning off said motor;
   means for biasing said lever member away from contact with said switching element, wherein said first actuating means and said second actuating means act upon said one lever member.

8. An injector as recited in claim 1 wherein said switching means comprises:
   a switching element;
   one lever member pivotally mounted adjacent to said switching element for contacting said switching element for turning off said motor;
   means for biasing said lever member away from contact with said switching element, wherein said first actuating means and said second actuating means act upon said one lever member.

9. An injector as recited in claim 1 wherein said resilient means is a tension device.

* * * * *